(12) United States Patent
Dakak (10) Patent No.: US 10,258,489 B2
(45) Date of Patent: Apr. 16, 2019

(54) ANGIOPLASTY ANCHOR AND/OR MARKER BALLOON STENT CATHETER APPARATUS AND METHOD

(71) Applicant: Nadar A. Dakak, Potomac, MD (US)

(72) Inventor: Nadar A. Dakak, Potomac, MD (US)

( * ) Notice: Subject to any disclaimer, the term of this patent is extended or adjusted under 35 U.S.C. 154(b) by 64 days.

(21) Appl. No.: 15/019,207

(22) Filed: Feb. 9, 2016

(65) Prior Publication Data

US 2017/0325979 A1    Nov. 16, 2017

(51) Int. Cl.

| | | |
|---|---|---|
| A61F 2/90 | (2013.01) | |
| A61F 2/954 | (2013.01) | |
| A61F 2/958 | (2013.01) | |
| A61M 25/10 | (2013.01) | |
| A61M 29/02 | (2006.01) | |
| A61F 2/962 | (2013.01) | |

(52) U.S. Cl.
CPC .............. *A61F 2/958* (2013.01); *A61F 2/954* (2013.01); *A61M 25/104* (2013.01); *A61M 29/02* (2013.01); *A61F 2/90* (2013.01); *A61F 2/962* (2013.01)

(58) Field of Classification Search
CPC ....... A61F 2/958; A61F 2/954; A61M 25/104; A61M 29/02

USPC ..................................................... 604/102.01
See application file for complete search history.

(56) References Cited

U.S. PATENT DOCUMENTS

| | | |
|---|---|---|
| 5,607,444 A | 3/1997 | Lam |
| 7,402,168 B2 * | 7/2008 | Sanderson .............. A61F 2/915 604/101.01 |
| 2007/0173784 A1 | 7/2007 | Johansson et al. |
| 2007/0270935 A1 | 11/2007 | Newhauser et al. |
| 2008/0086083 A1 | 4/2008 | Towler |
| 2008/0208307 A1 | 8/2008 | Ben-Muvhar et al. |
| 2008/0243233 A1 | 10/2008 | Ben-Muvhar et al. |
| 2009/0043194 A1 | 2/2009 | Barbut |

* cited by examiner

*Primary Examiner* — Phillip A Gray
(74) *Attorney, Agent, or Firm* — Houtteman Law LLC; Scott Houtteman; Bradford E. Kile (57) ABSTRACT

An angioplasty apparatus and method including a balloon stent, for facilitating accurate placement of a lumen stent for dilating a stenotic site, the apparatus includes arcuate, low pressure, anchor and/or marker and guide balloon segment(s) connected to a stent deployment catheter at at least one of a proximal and distal end of a wire mesh stent with circumferential gaps in the anchor and/or marker balloon segment or segments to facilitate blood flow and contrast media during a stenting procedure. Optimal positioning of a stent at a stenotic lumen site is facilitated by selective injection of marker fluid into one or more low pressure, anchor and/or marker balloon segment(s).

20 Claims, 5 Drawing Sheets

ANGIOPLASTY ANCHOR AND/OR MARKER BALLOON STENT CATHETER APPARATUS AND METHOD

RELATED APPLICATION

This application relates to co-pending applications entitled "Angioplasty Marker and Guide Catheter, With Bifurcation Site Stenting, Apparatus and Method," Ser. No. 15/019,183, and "Angioplasty, Self-Expanding, Stent Catheter With Low Pressure Anchor and/or Marker Balloon Assembly and Method," Ser. No. 15/019,237, both of common inventorship and ownership as the present application and as filed on an even date herewith. The disclosures of these co-pending applications are incorporated herein by reference as though set forth at length.

BACKGROUND OF THE DISCLOSURE

This invention relates to an anchor and/or guide balloon, stent catheter in the field of coronary and peripheral angioplasty. More specifically, this invention relates to accurate stent placement and balloon deployment at a stenotic site within a patient's vascular system, usually at a bifurcation site, while maintaining lumen access for insertion of marker fluid and blood flow during an angioplasty stenting procedure.

The vascular bed in humans is a complex and extensive network of lumens carrying blood and delivering oxygen and nutrients throughout the skeletal network, organs and muscle tissues of the body. At a macro level the human circulatory system can be logically characterized as originating from the heart with a briefly ascending aorta from the left ventricle upwardly into an arch and then descending generally vertically downward via a central lumen column through a patient's thoracic region and diaphragm to an abdominal aorta segment. The aorta terminates with common left and right iliac arteries extending into femoral arteries and down into popliteal arteries and distally to extremities of a patient's legs.

In general terms the aorta provides a base for systemic circulation for the entire body. Right and left coronary branches extend from an aortic root to supply a patient's heart while an aortic arch supplies blood to the patient's head, neck and arms. Branches from the thoracic aorta supply the chest and branches from the abdominal aorta supply the abdomen and kidneys while the pelvis and lower extremities are fed from common iliac arteries extending from a base region of the aorta.

The human vascular system, originating from the heart, is composed of a series of flexible lumens decreasing in diameter and increasing in branches. In broad terms a sequence of blood flow is from a left heart ventricle to an aorta, to arteries, to arterioles, to venules, to veins, and to a vena cava back to a right side of the heart.

Vascular lumens are composed of elastic tissue which can, over time, become somewhat hardened in a disease zone due to an internal accumulation of cholesterol laden plaque, which is a fatty material composed of cholesterol and other particles which build up within an artery wall to create a narrowing (stenosis) of the artery. Plaque stenotic segments can decrease vessel elasticity and concomitantly occlude a free flow of blood through the lumen. This malady is sometimes referred to as atherosclerotic arterial disease. Stenotic segments usually occur at lumen junction sites but can form at other locations throughout a human vascular system.

In 1964 an vascular radiologist by the name of Charles Dotter, often referred to as the "Father of Interventional Radiology" pioneered development of angioplasty and a catheter delivered stent as a treatment for peripheral arterial disease.

Stents are now universally used in percutaneous coronary and peripheral angioplasty procedures, which effectively open narrowed blood vessels. A stent is a tiny, expandable, cylindrical wire mesh scaffolding, which may be mounted on a deflated balloon in a "crimped" or collapsed state. A cylindrical stent scaffolding is inserted into a narrowed stenotic segment of an artery over a thin angioplasty guide wire via a catheter sheath and then expanded by inflating an internal, coaxial, cylindrical stent balloon.

A thin angioplasty guide wire is advanced, through the guide catheter, into a blood vessel and inserted through a narrowed lumen stenosis. A stent (with an interior, concentric, collapsed, tubular balloon) is introduced, over the angioplasty guide wire, through the guide catheter and accurately positioned at the lumen stenosis site. High pressure (nine to eighteen atmospheres) is then used to radially inflate the cylindrical balloon and permanently expand the wire stent scaffolding outwardly to radially expand and compress plaque at the lumen stenosis segment, resulting in a central enlarged opening inside the lumen for improved blood flow. The internal cylindrical balloon that is used to operably expand the stent is thereafter deflated and withdrawn along with the guide wire and catheter guide sheath while the expanded wire stent scaffolding remains positioned at the stenotic site.

An interventional physician uses radiography, an X-ray procedure, to identify a stenosis location and estimates the size of a diseased blood lumen and severity of stenotic plaque narrowing. Blood vessels are not visible by X-ray, per se, however, by injecting a contrast media (dye) through the catheter sheath a trained physician is capable of accurately viewing arterial boundaries carrying a pulsating flow of blood through the lumen and can develop an accurate sense of a stenotic site requiring interventional correction.

Placing a stent at a site of a stenosis in a downstream segment of a blood vessel is now considered a routine process. When plaque stenosis narrowing is located at a bifurcation opening of the blood vessel from the aorta, or at a downstream bifurcation site where a blood vessel branches, however, optimal placement of the stent is more challenging. In this, positioning a stent too distal may miss part of a narrowing stenosis while positioning a stent too proximal may result in proximal end of the stent protruding into a primary blood vessel.

Examples of challenging locations are plaque stenosis occurring at an opening of arteries originating from the aorta: the left main coronary artery, the right coronary artery, the innominate artery, left common carotid artery, left subclavian artery, celiac artery, superior mesenteric artery, inferior mesenteric artery, the left and right renal arteries and iliac arteries. Other examples include vessel bifurcations downstream in the coronary arterial tree such as the left anterior descending and the left circumflex coronary arteries which bifurcate from the left main coronary artery. It also includes peripheral arteries such as the common femoral arteries bifurcations.

Due to the complexity of accurately positioning a stent at a vessel bifurcation opening, in a pulsating circulatory system, stenting a stenosis at a bifurcation requires a longer operative time, exposing a patient and staff to extra radiation during the angiography, and injecting larger amounts of radiopaque contrast media which may compromise the patient's hemodynamic status and kidney functions. It is not uncommon for an interventional physician to use additional stents because of non-satisfactory initial results due to stent malposition. The procedure may therefore become prolonged and complex, carrying out higher risks and a higher rate of complications.

In order to address this problem it has been previously suggested to use a two part balloon stent catheter, where a relatively large torus part of a balloon is positioned at a proximal end of a cylindrical stent balloon. The inflated torus balloon serves as a stop at a bifurcation junction to prevent the stent on the cylindrical companion stent balloon from extending too far into a bifurcated lumen. At least one limitation of such a torus stop balloon, however, is that it will also temporarily limit or even occlude blood flow into a target vessel during stent positioning. It may also block a desired flow of contrast media (dye) from reaching a target vessel. In this, contrast media is often used to confirm the final positioning of the stent before radial deployment.

To address and ameliorate negative issues associated with a stop torus and concomitantly address a desire for a more sophisticated and accurate stent placement at stenotic bifurcation sites the subject invention is directed to a low pressure (one or two atmospheres) arcuate anchor and/or marker balloon segment or segments located at the proximal end of the stent balloon. The arcuate anchor and/or marker balloon segment (or segments) is separate from the cylindrical stent expansion balloon and will enable a free flow of blood and contrast media during a stenting procedure. In addition an arcuate anchor and/or marker balloon will provide a specific identification of a main vessel site to accurately position a conventional stent at the opening of the bifurcating vessel without protruding into the main vessel, using both angiography and tactile feedback, while reducing the use of contrast media.

Further although the subject anchor and/or marker system has primary function at a junction stenotic site frequently a straight vessel has small side branches, immediately before or after a stenosis. Inflating an anchor and/or marker balloon at a side branch, whether proximal or distal to the stenosis, can be used to localize the side branch cover it and protect it from getting covered when positioning a stent. This will also stabilize the stent prior to expansion in a pulsating arterial flow where the stent may be rocking back and forth during positioning due to pulsation blood flow. In this, if a stent is allowed to undesirably cover a side branch (sometimes referred to as jailing) blood flow to the side branch can be compromised.

The anchor and/or marker balloon segment (or segments) mounted on generally at a proximal or distal end of a stent is percutaneously inflated via a small independent tube or tubes within the deployment catheter using contrast media. By the provision of angiography and tactile feedback, a visible inflated marker and/or anchor and balloon at a proximal of the stent balloon is gently advanced and retracted to optimally face a stenotic site to be enlarged. Final balloon stent positioning may be confirmed by injection of contrast media via the guide catheter past the marker and/or anchor balloon segment or segments, before the stent balloon is inflated by application of internal high pressure.

Inflation pressure for the arcuate marker and/or anchor balloon segment or segments at a proximal or distal end of the stent is substantially less than the operating pressure of a conventional internal stent balloon. While a stent balloon needs a special inflation device to reach pressures between nine and eighteen atmospheres, the subject arcuate marker and/or anchor balloon segment or segments can be advantageously inflated to only one or two atmospheres by a hand syringe. Moreover, a blood lumen wall may, in some situations, have a curved or asymmetric geometry. A low pressure marker and/or anchor and guide balloon arcuate segment or segments can advantageously be used to facilely enhance alignment within a blood lumen wall by controlling the amount of pressure applied to a particular balloon segment or set of balloon segments in the marker and/or anchor and guide balloon(s).

The anchor and/or marker balloon segment or collectively segments do not extend a full three hundred and sixty degrees circumferentially around the deployment catheter. The arcuate shape of the subject low pressure marker and/or anchor and guide balloon segment or segments will accommodate and accurately identify a main vessel wall location, at a bifurcation of a blood vessel stenotic site. The arcuate shaped marker and/or anchor balloon segment or segments, in contrast to a full circumferential configuration, will advantageously not occlude blood flow to a target vessel and will concomitantly allow passage of contrast media during stent positioning.

The limitations suggested in the preceding are not intended to be exhaustive but rather are among many which may tend to reduce the effectiveness, reliability and physician/patient satisfaction with prior methods and apparatus for angioplasty, with stenting, at stenotic sites within a patient's circulatory system. Other noteworthy problems may also exist; however, those presented above should be sufficient to demonstrate that present angioplasty method and apparatus, involving stenting a stenotic lumen in a patient's vascular bed, appearing in the past will admit to worthwhile improvement.

THE DRAWINGS

Numerous advantages of the present invention will become apparent from the following detailed description of preferred embodiments taken in conjunction with the accompanying drawings wherein.

DETAILED DESCRIPTION

In this description the expression "approximately" or "generally" is intended to mean at or near but not always exactly such that an exact dimension or location is not considered critical in those contexts where those expressions appear. In this description focus will be directed to a vascular balloon stent mounted upon a deployment catheter sheath with an anchor and/or marker low pressure balloon segment or segments for angioplasty, with high pressure balloon stenting, at stenotic locations within a patient's vascular system. The terms "high" and "low" as used in this disclosure are mutually relative expressions. In a preferred embodiment "low" means approximately a pressure of one or two atmospheres while "high" means a pressure of nine to eighteen atmospheres, however, other relative pressures are within the scope of the subject disclosure.

Figures 1A, 1B:
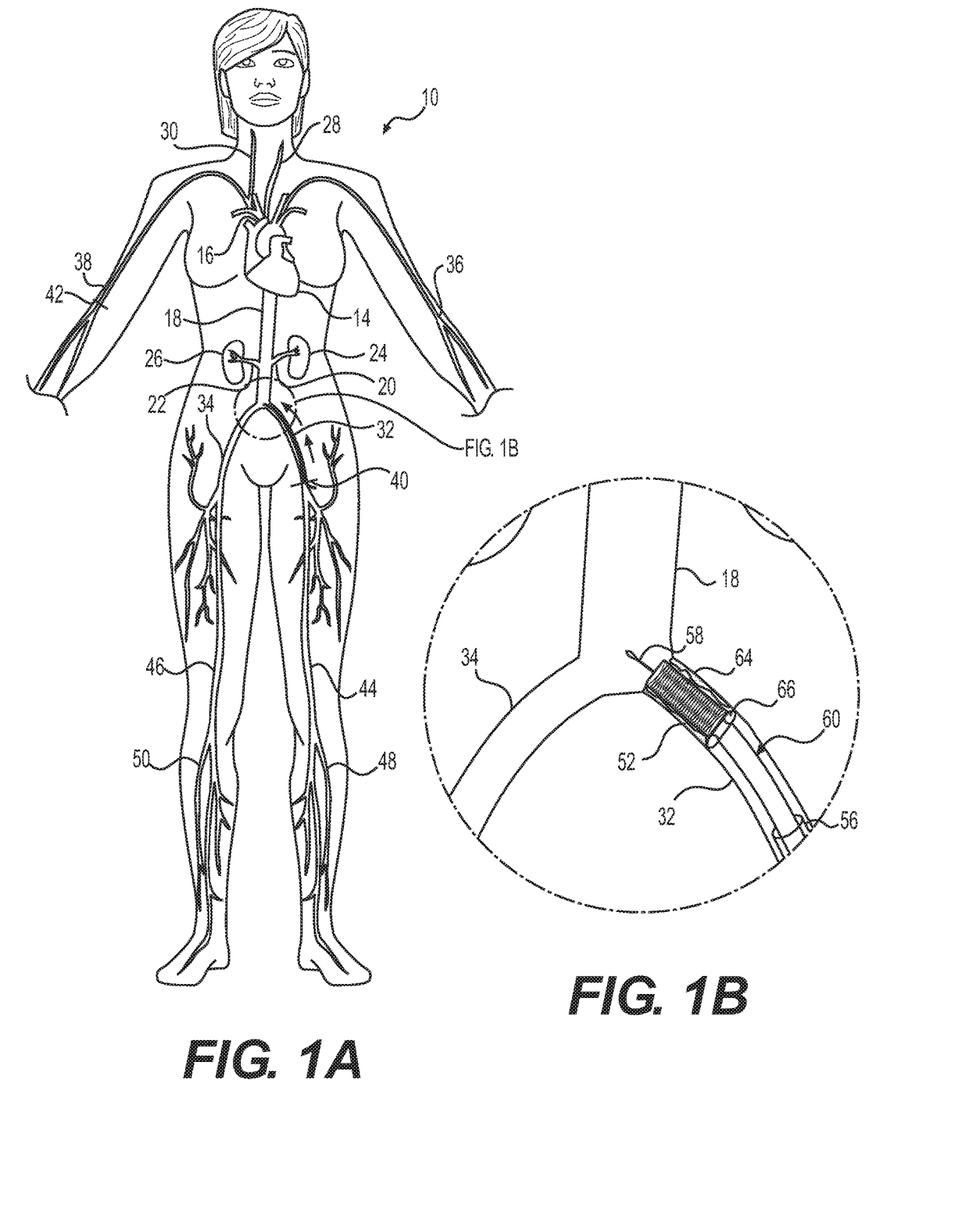
FIG. 1A is a generalized anatomic, silhouette, front view of basic components of a human with certain internal components of a circulatory system disclosed including a human heart and basic vascular bed with an illustrative insertion of a balloon stent deployment sheath into a patient's left leg common femoral artery to address an illustrative stenotic lesion at a junction of a patient's left external iliac artery and the base of the patient's aorta.
FIG. 1B is a bubble view of a balloon stent inserted into a patient's left common femoral artery to address a stenotic site at the junction of the patient's left iliac artery and the base junction with the patient's aorta as depicted in FIG. 1A.

Turning initially now to FIG. 1 there is shown a front view 10 of a human figure with outline images of generalized and basic components of a human vascular circulatory system including a heart 14, a briefly ascending aorta 16 stemming from to a left ventricle of the heart, and a descending abdominal aorta 18 with renal branch arteries 20 and 22 extending to left and right kidneys 24 and 26 respectively. As indicated above, the human body has a number of arteries stemming from the aorta but for purposes of this description only the renal arteries going to a patient's kidneys are depicted as being representative.

In addition to lateral left and right renal arteries extending from a patient's aorta to a human's kidneys, FIG. 1 generally depicts left and right carotid arteries 28 and 30 as well as left and right iliac arteries 32 and 34 which terminate at the common femoral arteries 40 which bifurcate to superficial femoral and profunda arteries which are illustrative of an artery bed in a human's lower vascular system. FIG. 1 also depicts left 36 and right 38 brachial arteries in the human figure's arms.

A conventional percutaneous entry site for angioplasty, with stenting, is in a patient's common femoral artery at approximately location 40 shown in FIG. 1 or in a brachial arm artery at approximately site 42 also depicted in FIG. 1.

As shown in FIG. 1B, if a stenosis 52 develops at the junction of a patient's left iliac artery with the base of the patient's aorta a guide wire 58 carrying a collapsed stent 64 may be operably inserted through the stenosis and the stent is brought into registry with the stenosis 52. The anchor and/or marker balloon segment(s) 66 is shown in an inflated posture to anchor the stent in position prior to radially deploying the stent by pressurizing an internal high pressure, cylindrical stent balloon. In addition marker media may be injection into the balloon segment(s) 66 to assist in accurately positioning the stent scaffolding 64.

Figure 2:
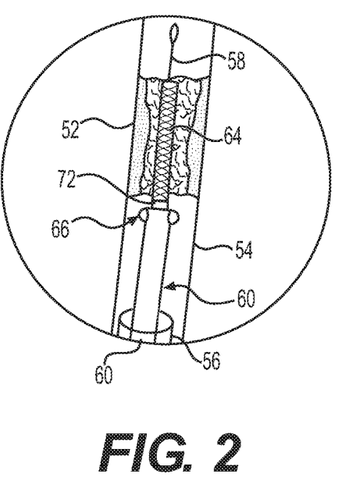
FIG. 2 is an illustrative detail view of a patient's blood lumen having a stenotic segment and introduction of a guide catheter carrying a guide wire and a surrounding balloon stent with a proximal low pressure anchor and/or marker balloon segment or segments.
Figure 3:
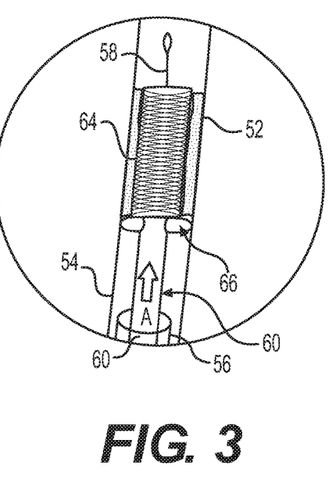
FIG. 3 is an illustrative detail view similar to FIGS. 2 and 1B of a human blood lumen wherein the proximal low pressure anchor and/or marker balloon segment or segments has been expanded to axially secure a balloon stent and an internal high pressure stent balloon that has been radially expanded to deploy a wire mesh stent against a stenotic site to enlarge the axial passage and facilitate a flow of blood through the lumen.
Figure 4:
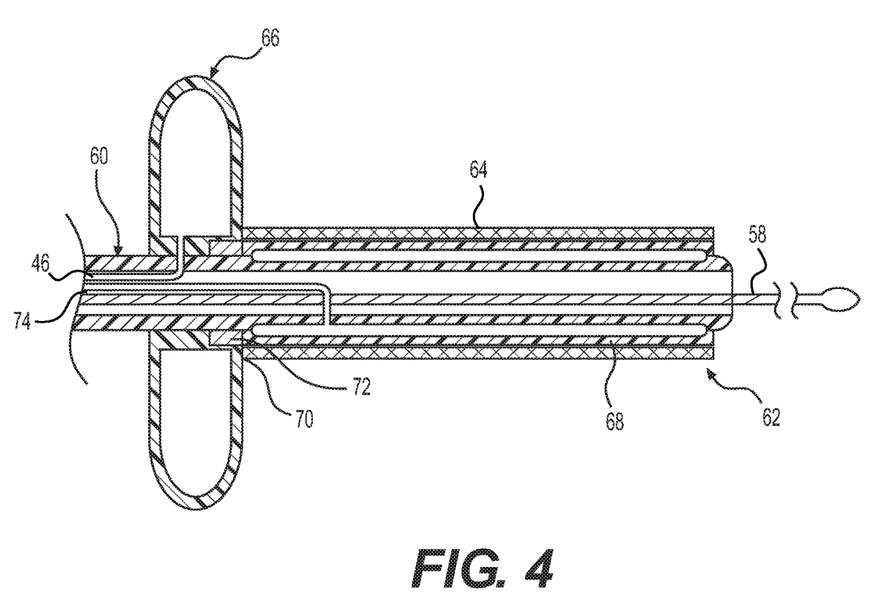
FIG. 4 is a cross-sectional detail view of a wire mesh stent and deployment catheter with a low pressure anchor and/or marker balloon segment(s) carried by the stent deployment catheter generally at a proximal end of the wire mesh stent.

Turning now to FIGS. 2-4 one preferred embodiment of the subject invention is depicted in further detail to address an issue of a stenosis site 52 within an artery lumen 54 of a human vascular bed. The specific site is not identified in FIGS. 2-3 and is intended to be generally illustrative of a number of stenosis locations that might develop within a human vascular bed. In FIG. 2 a catheter deployment sheath 56 is inserted into a patient's vascular lumen, via illustrative insertion sites 40 or 42 (note again FIG. 1). The deployment catheter 56 includes an entry check valve to enable a guide wire 58 and collapsed stent to be delivered into the patient's vascular system without permitting a back flow of blood from the entry site. The angioplasty guide wire 58 is trained through the catheter deployment sheath 56 and is further extended through the stenotic accumulation 52 to be treated.

A stent deployment sheath 60 is extended through the catheter deployment sheath 56, generally concentrically along the guide wire 58, to deliver a wire mesh stent 64, in a collapsed condition, into the heart of the stenotic site 52. An anchor and/or marker balloon segment 66, or segments, are mounted on the stent deployment sheath 60 generally at a proximal end 74 of the stent 64. The wire mesh stent 64 and anchor and/or marker balloon segment 66 (or segments) is delivered to a proximal end of the stenotic site to be treated through the catheter deployment sheath 56 in a collapsed condition as illustrated in FIG. 2.

On a stenotic site, FIG. 3 illustrates deployment of the low pressure, anchor and/or marker balloon segment 66 (or segments) via a low pressure inflation line 46 which can be an independent line, as illustrated in FIG. 4, or a line imbedded within the side wall of the stent deployment sheath 60. Axial positioning of the collapsed wire mesh stent 64 can be facilitated by registry of a radiopaque marker band 72 located generally at a proximal end of the stent 64, note as an example FIG. 2, or by injecting radiopaque dye through the axial opening provided by the stent guide balloon segment 66 or (segments).

As further illustrated in FIGS. 3-4, once the wire mesh stent 64 is axially positioned within a stenotic site 52 to be treated an internal, coaxial, cylindrical balloon 68, note particularly FIG. 4, is injected with a high pressure fluid in a range of nine to eighteen atmospheres via an independent high pressure line 74, or a line embedded within the sidewall of the deployment sheath 60, to radially expand the surrounding wire mesh stent 64 outward to open the stenotic site 52 and restore an open lumen 54 for normal blood circulation. Following deployment the wire mesh stent 64 will remain within a patient's lumen 54 as a scaffolding to keep an open flow channel through the stenotic site.

Figure 5A:
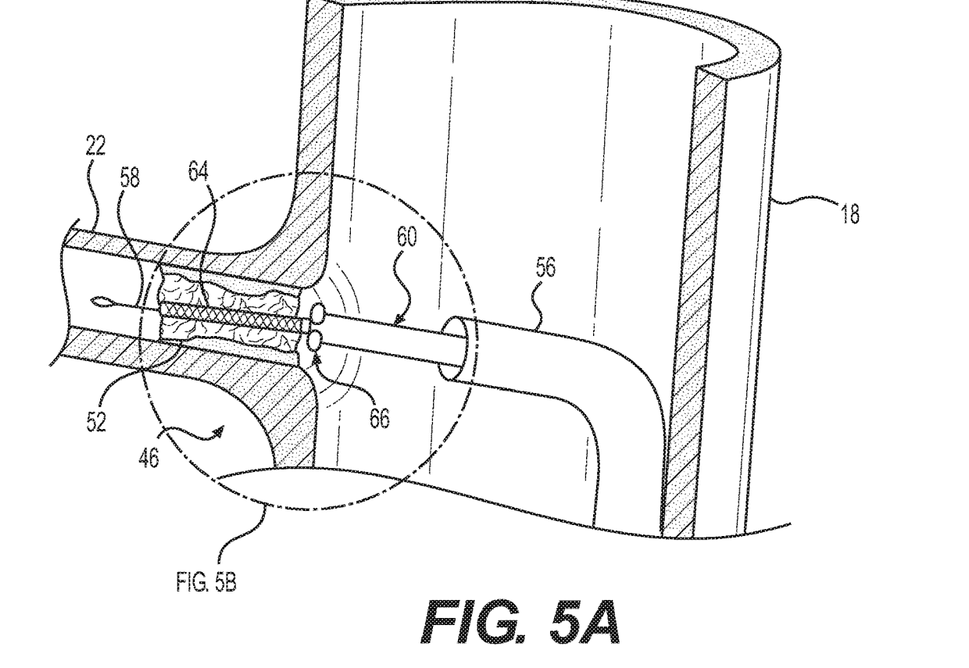
FIG. 5A is a partial detail view of an illustrative segment of a patient's aorta and lateral extending renal artery branch where a stenotic lesion has formed at the junction and with initial introduction of a balloon stent and an anchor and/or marker balloon mounted at a proximal end of the stent.
Figure 5B:
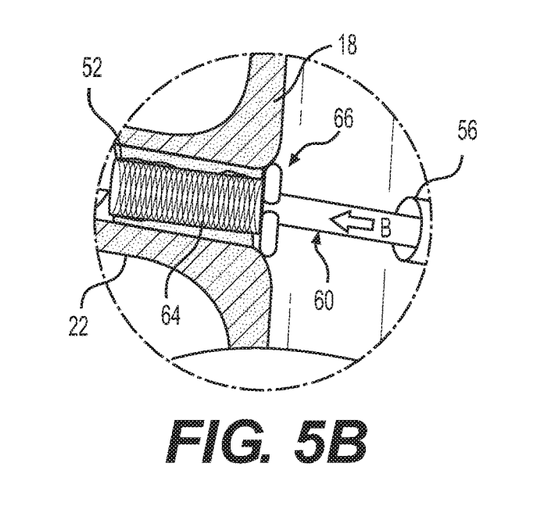
FIG. 5B is a bubble detail view of the stent depicted in FIG. 5A where the anchor and/or marker balloon segment has been expanded and the stent 64 has also been expanded against a stenotic site to enlarge the junction opening of the renal artery from the patient's aorta.

Turning to FIGS. 5A and 5B a stenotic site 52 is shown as an accumulation at a junction location of a patient's aorta 18 and right renal artery 22. At this illustrative stenotic damaged site a guide catheter 56 is used to introduce a collapsed balloon stent 64 carried by a guide wire 58 into and through the stenosis 52. Once generally positioned anchor and/or marker balloon segment(s) 66 are expanded by the introduction of a relatively low pressure saline or marker fluid as illustrated in FIG. 5B. The expanded anchor and/or marker balloon segment(s) 66 serve to abut against the junction site and a proximal end of the stenosis and effectively assist in properly positioning the balloon stent 64 axially within the stenosis 52. Once axially positioned the internal cylindrical, high pressure, stent balloon is deployed and the stent 64 is radially expanded against the stenosis to open the site and create a scaffolding structure to keep the site opened to facilitate blood flow into the renal artery.

Figure 6:
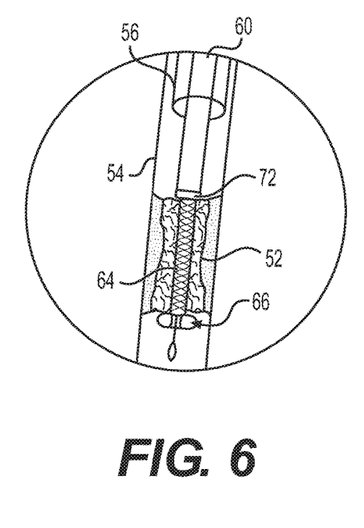
FIG. 6 is an illustrative detail view, similar to FIG. 2 of a human blood lumen having a stenotic segment and introduction of a guide catheter carrying a guide wire and a surrounding balloon stent with a distal low pressure anchor and/or marker balloon segment or segments.
Figure 7:
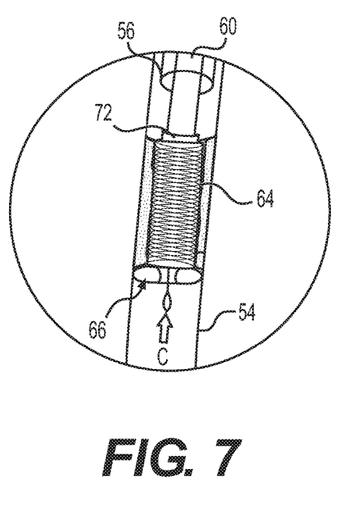
FIG. 7 is an illustrative detail view similar to FIG. 3 of a human blood lumen wherein the low pressure anchor and/or marker balloon segment or segments at a distal end of a stent has been expanded to axially secure the balloon stent and an internal high pressure stent balloon has been radially expanded to deploy a wire mesh stent against a stenotic site to enlarge the site for axial passage to facilitate blood flow through the lumen.
Figure 8:
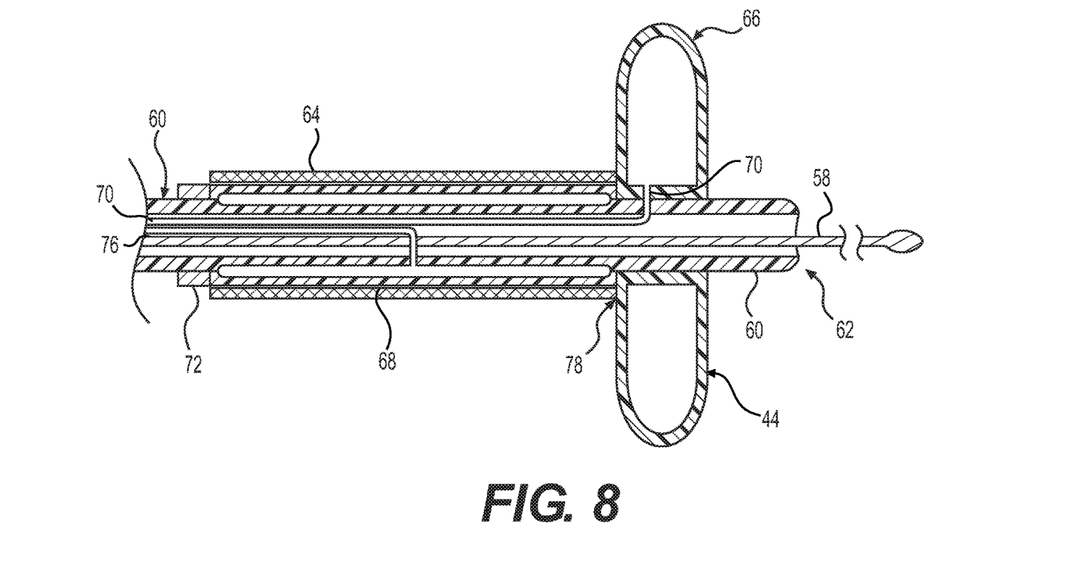
FIG. 8 is a view similar to FIG. 4 disclosing a cross-sectional detail view of a wire mesh stent and deployment catheter with a low pressure anchor and/or marker balloon segment(s) carried by the deployment catheter generally at a distal end of the wire mesh stent.

Referring now to FIGS. 6-8 there is illustrated another preferred embodiment of the invention where a guide balloon segment 66 (or segments) is mounted on the deployment catheter 60 generally at a distal location 78 of the wire mesh stent 64. In a manner similar to the description of the stent 64 illustrated and described in connection with FIGS. 2-4 the anchor and/or marker balloon segment 66 (or segments) positioned at a distal end of the wire mesh stent 64 is operable to anchor, guide and locate the wire mesh stent 64 within a stenotic site 52 for deployment and radial expansion of the stent to enlarge the stenotic site 52 and restore a flow of blood through a partially occluded blood lumen. The difference between FIGS. 2-4 and FIGS. 5-7 is the axial location of the anchor and/or marker balloon segment 66 or segments with respect to the stent 64. In this, FIGS. 2-4 depict the anchor and/or marker balloon segment(s) in as posture proximal to the stent 64 while FIGS. 6-8 disclose the anchor and/or marker balloon segment(s) distal to the stent 64.

Referring specifically to FIGS. 6-7, once the wire mesh stent 64 is axially positioned with respect to a stenotic site 52 the low pressure anchor and/or marker balloon segment 66 (or segments) is expanded via a low pressure inflation line 46 in FIGS. 4 and 70 in FIG. 8 to secure the stent 64 axially in an optimum posture. Then high pressure fluid is injected via line 74 in FIGS. 4 and 76 in FIG. 8 into the cylindrical, expansion balloon 68 to radially deploy the wire mesh stent 64 radially outward as illustrated in FIGS. 3 and 7.

Figures 9, 10, 11:
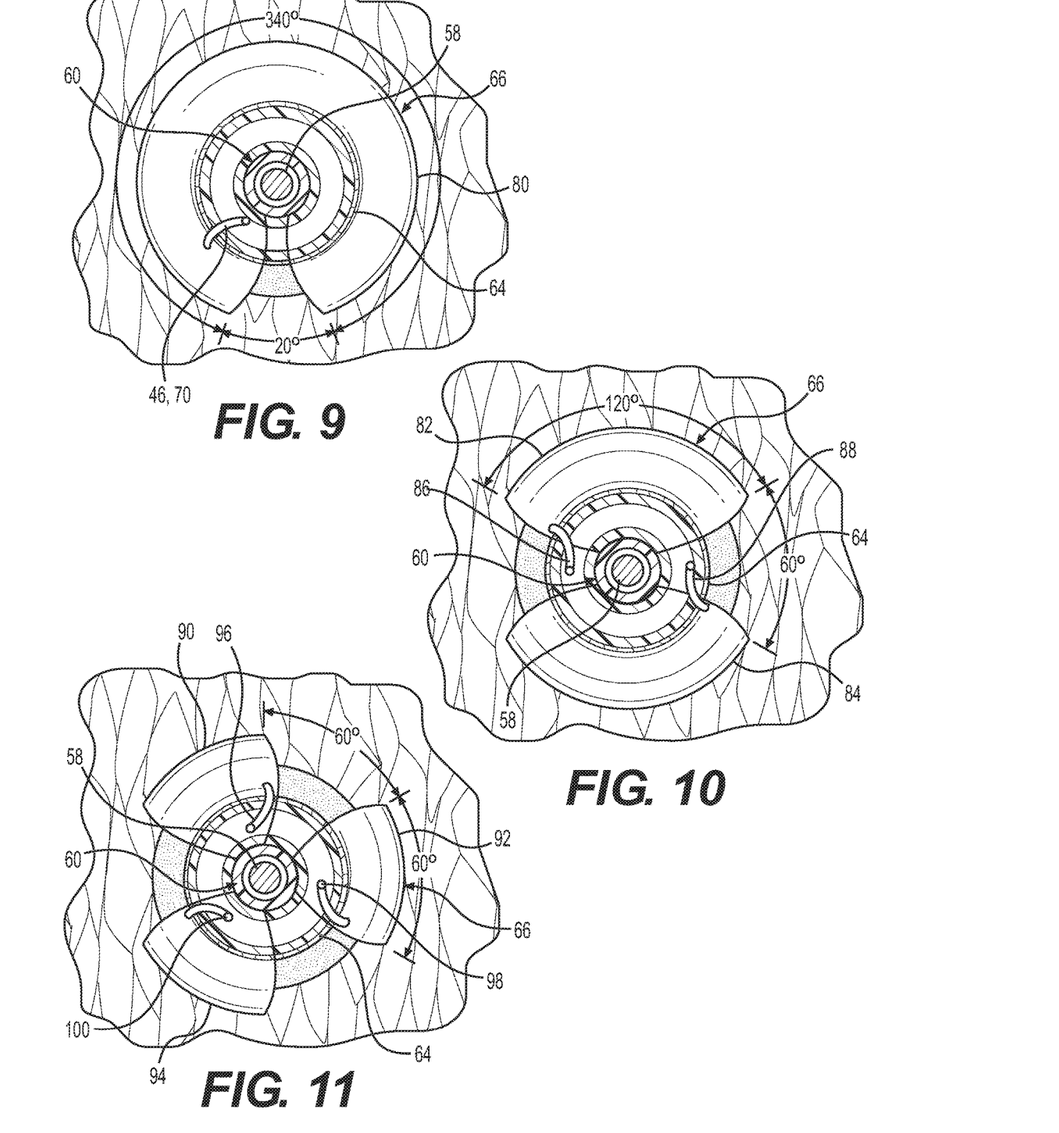
FIG. 9 is an end and partial cross-sectional view taken in the direction of arrow "A" in FIG. 3, arrow "B" in FIG. 5B and "C" in FIG. 7 disclosing one embodiment of an anchor and/or marker balloon assembly.
FIG. 10 is an end and partial cross-sectional view similar to FIG. 9 disclosing another embodiment of the invention where two opposing and generally equally angular anchor and/or marker balloon segments of approximately one hundred and twenty degrees are illustrated positioned about a balloon stent deployment sheath to advantageously maintain blood flow during a stenting procedure.
FIG. 11 is a view similar to FIGS. 9 and 10 disclosing yet another embodiment of the invention where three generally symmetrically disposed and opposing anchor and/or marker balloon segments of approximately sixty degrees each are illustrated positioned about a balloon stent deployment catheter to advantageously maintain blood flow during a stenting procedure.

Viewed in the direction of arrow "A" in FIG. 3, "B" in FIG. 5B and similarly "C" in FIG. 7, FIG. 9 depicts one preferred embodiment of the low pressure, anchor and/or marker balloon segment 66. More specifically, a single low pressure, arcuate, anchor and/or marker balloon 80 that preferably extends approximately three hundred and forty degrees around a distal end of the stent deployment sheath 60. The single low pressure, anchor and guide balloon segment 80 has a small, low pressure line 46, 70 that extends along or within the stent deployment sheath 60 and is used to inflate the anchor and/or guide balloon segment 80. At a location exterior to a patient's vascular system a physician is able to inject low pressure (one or two atmospheres) radiopaque media into anchor and/or marker balloon segment 80 by injection from a hand syringe (not shown). Although the exterior surface of the anchor and/or marker and guide balloon 80 is illustrated with a smooth exterior surface in certain instances it is contemplated that elevated transverse ridges, cross-hatching ridges or dimples can be formed on the exterior surface of the balloon segment 80 to facilitate the anchor function of the low pressure balloon segment.

The anchor and/or marker balloon segment 80 preferably occupies an arcuate expanse of approximately three hundred and forty degrees so that there is a minimal gap of at least approximately twenty degrees past the anchor and guide balloon 80 for passage of blood or contrast media through an artery during a stenting procedure. Although three hundred and forty degrees is preferred for the arcuate extent of the anchor and/or marker balloon segment 80 a degree of operative advantage can be realized by the subject invention where the arcuate extent of the single anchor and/or marker balloon segment 80 shown in FIG. 9 is as little as forty five degrees.

FIG. 10 is a view similar to FIG. 9 but discloses an alternate preferred embodiment of the invention disclosing a low pressure anchor and guide balloon system 66 including placement of two, arcuate, low pressure anchor and guide balloon segments 82 and 84 positioned in an opposing posture at a proximal (FIGS. 2 and 5A) or distal (FIG. 6) end of the wire mesh stent 64. This balanced arrangement of arcuate marker balloon segments, which can be independently inflated with marker fluid, enhances an ability to establish approximately coaxial placement of the opening of a wire mesh stent 64 within a stenotic site 52. In this embodiment each of the two balloon segments subtends an angle of at least one hundred degrees but less than one hundred and forty degrees and preferably one hundred and twenty degrees. The substantial open regions of approximately eighty to one hundred and sixty degrees provides relatively unobstructed blood and contrast media flow past the anchor and/or marker and guide balloon segments 82 and 84 during a stenting procedure.

Each of the marker balloon arcuate segments is fitted with an independent thin tube 86 and 88 extending through the stent deployment sheath 60 for use in independently inflating the low pressure anchor and/or marker balloon segments 82 and 84 with a radiopaque or saline fluid by using a syringe. The capacity and capability to separately inflate each anchor and/or marker balloon segment 82 and 84 enables a physician to selectively orient and guide the end of the stent deployment sheath 60 within a patient's lumen.

FIG. 11 discloses yet another preferred embodiment of the anchor and/or marker balloon segments 66. In this embodiment three approximately uniform, arcuate, anchor and/or marker and guide balloon segments are composed of low pressure balloons 90, 92, and 94 and independent corresponding inflation lines 96, 98, and 100. This enables transmission of a low pressure radiopaque marker media or saline solution via a syringe to the anchor and/or marker balloon segments generally at a proximal end (note FIGS. 2 and 5A) or distal end (note FIG. 6) but in each instance separate from the high pressure, stent deployment balloon 68. The anchor and/or marker balloon segments 90, 92, and 94 each extend peripherally around the stent deployment sheath 60 at least approximately twenty degrees but less than one hundred degrees and preferably sixty degrees around the stent deployment sheath 60. In this embodiment it is preferred that there is symmetric positioning of the anchor and/or marker balloon segments. This preferred anchor and/or marker balloon spacing concomitantly provides at least approximately sixty degrees of open space for blood and contrast media flow during a stenting procedure and with three independent pressure zones a capacity for enhanced positioning capability of a of the stent deployment by appropriate selection of pressure within each anchor and/or marker and guide balloon segment 90, 92 and 94.

In operation, a syringe is preferably used to inflate the low pressure anchor and/or marker balloon segment 66 (or segments) with a radiopaque marker media or saline solution. A balloon stent 64 is slid over the guide wire 58 extending generally coaxially within the interior of the guide catheter 56. A radiopaque marker band 72 is positioned in the region of a lumen stenosis 52 to be treated, as illustrated in FIGS. 2, 5A and 6.

When a stenotic site is at an origin of a blood vessel from the aorta, FIGS. 5A and 5B, the thin angioplasty guide wire 58 is advanced via the guide catheter 56, crossing the site of a stenosis into a downstream vessel. The stent 64 is then advanced over the guide wire 58 and into the stenotic site. When the stent is mostly inside the stenotic site, yet with the radiopaque marker band 72, still outside, the guide catheter tip is slightly pulled back into the aorta, the anchor and/or radiopaque marker balloon segments are inflated and gently advanced to face the opening of a blood vessel to be treated. Position is confirmed by tactile feedback and contrast media injection. The high pressure stent balloon 68 is then inflated and the stent 64 is radially deployed. After the stent 64 is set the anchor and/or marker balloon segment(s) and the stent balloon are deflated and the guide wire 58, anchor and/or marker balloon segment(s) 66, stent balloon 48 and stent catheter sheath 56 are all withdrawn.

When a lesion to be treated is downstream in the blood vessel FIGS. 2 and 3, and the radiopaque marker 72 or low pressure marker balloon segment 66 (or segments) containing a radiopaque fluid reaches a stenotic site a physician accurately knows that the stent 64 is in a proper posture for deployment. At this point the interior stent balloon 68, note FIG. 4, is inflated with approximately nine to eighteen atmospheres of pressure to expand the wire stent scaffolding 64 as shown in FIGS. 3 and 7. Once expanded the plaque stenosis 52 is pushed outwardly allowing the damaged site to be radially enlarged about the stent scaffolding to restore a flow of blood through the stenotic site.

The arcuate, anchor and/or marker, balloon segment gap(s) enables blood perfusion to through a diseased vessel during a stenting procedure and concomitantly allows contrast media flow to confirm final stent axial position before deployment.

When injecting radiopaque media through the guide catheter 56 radiopaque contrast media passes between the anchor and guide balloon segment(s) and into side branch lumens thus providing a view of the downstream side vessel geometry and confirming a desired position of the anchor and/or marker balloon segment (segments) and stent.

In general the low pressure anchor and guide balloon(s) will cover varying degrees of the blood vessel opening, and the degree of coverage and anchor and guide balloon pressure may vary to allow matching a branching angle, such as when positioning a stent at a bifurcation that is less than 90 degrees. This might occur at the bifurcation of the abdominal aorta into the iliac arteries and the bifurcation of the common femoral arteries. In these instances the interventional physician, may prefer an anchor and/or marker balloon extending less than one hundred and eight degrees, in a way that the marker balloon will fall on the shoulder of the bifurcation, rather in the lumen of the branching vessel.

The low pressure anchor and/or marker balloon segment or segments outer cross sectional diameter is larger than the diameter of the target vessel but smaller than the diameter of the application artery to allow proper inflation at a bifurcation FIG. 5B. When the stenosis is downstream with respect to a blood vessel the diameter will match the diameter of the target vessel, note FIGS. 3 and 7. Moreover the exterior of the anchor and/or marker and guide balloon segment (segments) 66 can be operable textured by a raised rib or pebble pattern to assist in an anchor function at a downstream stenotic site.

The advantages provided by a low pressure anchor and/or marker balloon segment or segments mounted on a proximal or distal end of a wire mesh stent facilitates, for example, accurate positioning of a stent within a patient's vascular system. In this context the low pressure balloon anchor and guide balloon segment or segments permits both a flow of blood during a stenting procedure and also a flow of radiopaque marker media to facilitate accurate placement of a stent at a stenosis site. Although the structure of a low pressure marker balloon segment (or segments) are depicted, for example, in FIGS. 9-11, it will be appreciated by those skilled in the art that the physical size of the arcuate anchor and/or marker balloon segment, and arcuate anchor and/or marker and guide balloon segments may be selected to suit the anatomy of a patient of interest.

In describing the invention, reference has been made to preferred embodiments. Those skilled in the art however, and familiar with the disclosure of the subject invention, may recognize additions, deletions, substitutions, modifications and/or other changes which will fall within the scope of the invention as defined in the following claims.

What is claimed is:

1. An angioplasty balloon stent catheter apparatus for facilitating accurate placement of a balloon stent within a patient's stenotic lumen site, said angioplasty balloon stent catheter apparatus comprising:
   a deployment catheter having a proximal end and a distal end and being operable to be extended over a guide wire during a patient stenting procedure;
   a balloon catheter stent connected generally at a distal end of said deployment catheter, said balloon catheter stent having,
      a generally cylindrical wire mesh stent operable for deployment and expansion at a stenotic site within a human blood lumen,
      a generally cylindrical high pressure balloon extending coaxially within the interior of said generally cylindrical wire mesh stent, said high pressure balloon being operable to radially expand said wire mesh stent within a patient's stenotic blood lumen site;
   a low pressure guide balloon assembly connected to said deployment catheter, said guide balloon assembly including,
      one or more inflatable low pressure arcuate balloon segments,
      at least one of said inflatable low pressure arcuate balloon segments having a total circumferential extent less than or equal to three hundred forty degrees extending about said deployment catheter, and said at least one of said inflatable low pressure arcuate balloon segments being generally axially located on said deployment catheter at at least one of a distal end and a proximal end of said balloon catheter stent but slightly axially separate from said stent; and at least one low pressure inflation conduit connected to at least one of said inflatable low pressure arcuate balloon segments and being operable to be connected to a low pressure inflation source at a proximal end of said deployment catheter for selective delivery of fluid under low pressure to said at least one of said inflatable low pressure arcuate balloon segments, and wherein at least one of said inflatable low pressure arcuate balloon segments subtends an arc of at least approximately twenty degrees.

2. An angioplasty balloon stent catheter apparatus as defined in claim 1 wherein said arcuate shaped balloon segment is mounted on said deployment catheter:
at a generally proximal end of said stent.

3. An angioplasty balloon stent catheter apparatus as defined in claim 1 wherein said arcuate shaped balloon segment is mounted on said deployment catheter:
at a generally distal end of said stent.

4. An angioplasty balloon stent catheter apparatus as defined in claim 1 wherein said balloon assembly having at least one inflatable arcuate balloon segment and inflatable arcuate balloon segments comprises:
an arcuate shaped balloon segment mounted generally at a distal end of said deployment catheter sheath, said arcuate shaped balloon segment subtends an arc of at least approximately three hundred forty degrees.

5. An angioplasty balloon stent catheter apparatus as defined in claim 4 wherein said arcuate shaped balloon segment mounted generally at a distal end of said deployment catheter sheath is mounted on said deployment catheter sheath:
at a generally proximal end of said balloon catheter stent.

6. An angioplasty balloon stent catheter apparatus as defined in claim 4 wherein said arcuate shaped balloon segment mounted generally at a distal end of said deployment catheter sheath is mounted on said deployment catheter sheath:
at a generally distal end of said balloon catheter stent.

7. An angioplasty balloon stent catheter apparatus as defined in claim 1 wherein said guide balloon assembly having at least one inflatable arcuate balloon segment and inflatable arcuate balloon segments comprises:
each of said plurality of arcuate shaped balloon segments subtends an arc of at least approximately twenty degrees.

8. An angioplasty balloon stent catheter apparatus as defined in claim 7 wherein said guide balloon assembly having at least one of said inflatable arcuate balloon segments comprises:
at least two independent and symmetrically opposing arcuate shaped balloon segments mounted on said deployment catheter.

9. An angioplasty balloon stent catheter apparatus as defined in claim 8 wherein:
each of said two independent and symmetrically opposing arcuate shaped segments mounted generally at the distal end of said catheter assembly subtends an arc of at least approximately one hundred degrees.

10. An angioplasty balloon stent catheter apparatus as defined in claim 8 wherein:
each of said two independent and symmetrically opposing arcuate guide balloon segments generally at the distal end of said catheter assembly subtends an arc of at least approximately one hundred and twenty degrees.

11. An angioplasty balloon stent catheter apparatus as defined in claim 7 wherein said balloon assembly having at least one inflatable arcuate balloon segment and inflatable arcuate balloon segments comprises:
at least three independent and symmetrically opposing arcuate shaped balloon segments mounted on said deployment catheter sheath generally at a distal end of said balloon catheter stent.

12. An angioplasty balloon stent catheter apparatus as defined in claim 11 wherein:
each of said three independent and symmetrically opposing arcuate shaped balloon segments mounted at a distal end of said balloon catheter stent subtends an arc of at least twenty degrees.

13. An angioplasty balloon stent catheter apparatus as defined in claim 11 wherein:
each of said at least three independent and symmetrically opposing arcuate shaped balloon segments mounted on said deployment catheter sheath generally at the distal end of said balloon catheter stent subtends an arc of at least sixty degrees.

14. An angioplasty balloon stent catheter apparatus as defined in claim 11 wherein:
each of said three independent and symmetrically opposing arcuate shaped balloon segments mounted on said deployment catheter sheath generally at the distal end of said balloon catheter stent subtends an arc of at least one hundred degrees.

15. An angioplasty apparatus, with balloon stent, for facilitating accurate placement of a lumen stent for dilating a patient's stenotic site, said angioplasty apparatus comprises:
a percutaneous deployment catheter having a proximal end and a distal end, wherein said distal end is operable to be threaded over a guide wire positioned within a patient's lumen to be treated;
a balloon, wire mesh, stent assembly mounted generally at a distal end of said deployment catheter, said balloon, wire mesh, stent assembly including,
an expandable wire mesh stent, and
a high pressure, generally cylindrical balloon mounted concentrically within said expandable wire mesh stent for selectively expanding said wire mesh stent at a stenotic site within a patient's lumen; and
a balloon assembly mounted upon said percutaneous deployment catheter generally at at least one of a distal end and a proximal end of said stent assembly, said balloon assembly including,
at least one low pressure arcuate balloon segment having a total circumferential extent less than or equal to three hundred and forty degrees for facilitating blood flow through a patient's lumen during a stenting procedure, and
said at least on low pressure arcuate balloon segment further comprises two independent and symmetrically opposing low pressure arcuate balloon segments mounted generally at a distal end of said deployment catheter, and
each of said balloon segments subtends an arc of at least twenty degrees.

16. An angioplasty apparatus, with balloon stent, for facilitating accurate placement of a lumen stent and dilating a stenotic site as defined in claim 15 wherein said balloon assembly includes:

an independent low pressure inflation conduit connected to each of said low pressure arcuate balloon segments to independently inflate said balloon segments to facilely conform said inflated balloon segments to a stenotic lumen site.

17. An angioplasty apparatus, with balloon stent, for facilitating accurate placement of a lumen stent and dilating a stenotic site as defined in claim 16 wherein said balloon assembly further comprises:

each of said two independent and symmetrically opposing low pressure arcuate balloon segments subtends an arc of at least approximately one hundred and twenty degrees.

18. An angioplasty apparatus, with balloon stent, for facilitating accurate placement of a lumen stent and dilating a stenotic site as defined in claim 15 wherein said balloon assembly having at least one of a low pressure inflatable balloon segment and low pressure balloon segments further comprises:

at least three independent and symmetrically positioned, low pressure, arcuate balloon segments mounted generally at a distal end of said deployment catheter sheath wherein each of said arcuate balloon segments subtends an arc of at least approximately sixty degrees.

19. An angioplasty apparatus, with balloon stent, for facilitating accurate placement of a lumen stent and dilating a lumen stenotic site as defined in claim 18 wherein said balloon assembly having at least one low pressure inflatable balloon segment and low pressure, inflatable segments includes:

an independent low pressure inflation conduit connected to each of said low pressure balloon segments to independently inflate said at least three low pressure anchor and guide balloon segments to facilely conform said inflated balloon segments at a stenotic lumen site.

20. An angioplasty apparatus, with balloon stent, for facilitating accurate placement of a lumen stent and dilating a lumen stenosis as defined in claim 19 wherein said balloon assembly having at least one low pressure, inflatable balloon segment and low pressure, inflatable balloon segments comprises:

each of said at least three independent and symmetrically opposing arcuate balloon segments mounted generally at the distal end of said deployment catheter assembly subtends an arc of at least approximately one hundred degrees.

* * * * *